US012678469B2

(12) United States Patent
Ahn et al.

(10) Patent No.: US 12,678,469 B2
(45) Date of Patent: Jul. 14, 2026

(54) MICROORGANISM WITH HIGH TRIPEPTIDE PRODUCTIVITY AND USE THEREOF

(71) Applicant: SAMYANG CORPORATION, Seoul (KR)

(72) Inventors: Sin Hye Ahn, Goyang-si (KR); Bu-Soo Park, Hanam-si (KR); Sanghee Lee, Gwangju-si (KR); Chong Jin Park, Seoul (KR); Eunsoo Choi, Seongnam-si (KR); Soun Gyu Kwon, Gwangmyeong-si (KR)

(73) Assignee: SAMYANG CORPORATION, Seoul (KR)

( * ) Notice: Subject to any disclaimer, the term of this patent is extended or adjusted under 35 U.S.C. 154(b) by 345 days.

(21) Appl. No.: 18/265,426

(22) PCT Filed: Dec. 1, 2021

(86) PCT No.: PCT/KR2021/017985
§ 371 (c)(1),
(2) Date: Jun. 5, 2023

(87) PCT Pub. No.: WO2022/131623
PCT Pub. Date: Jun. 23, 2022

(65) Prior Publication Data
US 2025/0262258 A1      Aug. 21, 2025

(30) Foreign Application Priority Data
Dec. 17, 2020      (KR) ........................ 10-2020-0177834

(51) Int. Cl.
*A61K 36/062* (2006.01)
*C07K 5/02* (2006.01)
*C12N 1/165* (2026.01)
*C12N 9/04* (2006.01)
*C12R 1/72* (2006.01)

(52) U.S. Cl.
CPC .......... *A61K 36/062* (2013.01); *C07K 5/0215* (2013.01); *C12N 1/165* (2021.05); *C12N 9/0006* (2013.01); *C12R 2001/72* (2021.05); *C12Y 101/01001* (2013.01)

(58) Field of Classification Search
CPC ...... C12N 15/81; C12N 15/815; C12N 1/165; C12N 9/0006; C07K 5/0215; C12P 21/02; C12Y 101/01001; A61K 36/062; A61K 36/06; A61P 1/16; A61P 3/10; A61P 9/00
See application file for complete search history.

(56) References Cited

FOREIGN PATENT DOCUMENTS

| CN | 101880702 | 12/2012 |
| CN | 105255748 | 11/2018 |
| KR | 10-2005-0027009 | 3/2005 |
| KR | 10-2011-0118492 | 10/2011 |

(Continued)

OTHER PUBLICATIONS

Liang et al., (Enzyme and Microbial Technology 42(3):284-289. Feb. 2008). (Year: 2008).*

(Continued)

*Primary Examiner* — Jana A Hines
(74) *Attorney, Agent, or Firm* — LEX IP MEISTER, PLLC

(57) ABSTRACT

The present invention relates to a *Candida utilis* strain having high tripeptide-producing ability and/or alcohol lyase activity and its use.

6 Claims, 5 Drawing Sheets

Specification includes a Sequence Listing.

(56) References Cited

FOREIGN PATENT DOCUMENTS

| KR | 10-2017-0026266 | 3/2017 | |
| WO | WO-2012097091 A2 * | 7/2012 | ............... C12N 9/92 |
| WO | 2019139031 | 7/2019 | |

OTHER PUBLICATIONS

JPO, Office Action of JP 2023-536882 dated Jul. 23, 2024.

Yin Li et al., "Glutathione: a review on biotechnological production", Appl Microbiol Biotechnol., vol. 66, pp. 233-242 (2004), Oct. 12, 2004. https://doi.org/10.1007/s00253-004-1751-y.

F. Domenech et al., "Ethanol utilization for metabolite production by Candida utilis strains in liquid medium", Acta Biotechnol., 1999, vol. 19, issue 1, pp. 27-36, Feb. 2, 2004.

KIPO, PCT Search Report & Written Opinion of PCT/KR2021/017985 dated Mar. 8, 2022.

Brown, Steven D., et al. "Mutant alcohol dehydrogenase leads to improved ethanol tolerance in Clostridium thermocellum." Proceedings of the National Academy of Sciences 108.33 (Aug. 16, 2011): 13752-13757.

Park, Yong-Cheol, et al. "Molecular cloning and characterization of the alcohol dehydrogenase ADH1 gene of Candida utilis ATCC 9950." Journal of Industrial Microbiology and Biotechnology 33.12 (Jul. 20, 2006): 1032-1036.

Olga de Smidt et al., "The alcohol dehydrogenases of Saccharomyces cerevisiae: a comprehensive review", FEMS Yeast Res, vol. 8, May 8, 2008, 967-978.

Dorota Grabek-Lejko et al., "Alcoholic fermentation by wild-type Hansenula polymorpha and Saccharomyces cerevisiae versus recombinant strains with an elevated level of intracellular glutathione", J Ind Microbiol Biotechnol (2011) 38:1853-1859, Apr. 29, 2011.

Jae-Young Cha et al., "Alcoholic Hepatotoxicity Suppression in Alcohol Fed Rats by Glutathione-enriched Yeast FF-8 Strain", Food Sei. Biotechnol. vol. 18, No. 6, pp. 1411 ~ 1416, Dec. 31, 2009.

Narisu et al., "Screening and identification of yeast for tolerance to high temperature, alcohol and low acid", Pratacultural Science, vol. 30, No. 10, total 8 pages, 2013.

Wu Gui-ying et al., "Study on fermentation conditions of alcohol dehydrogenase from Saccharomyces cerevisiae", Science and Technology of Food Industry, vol. 30, No. 11, 2009, total 3 pages.

* cited by examiner

【Fig. 1】
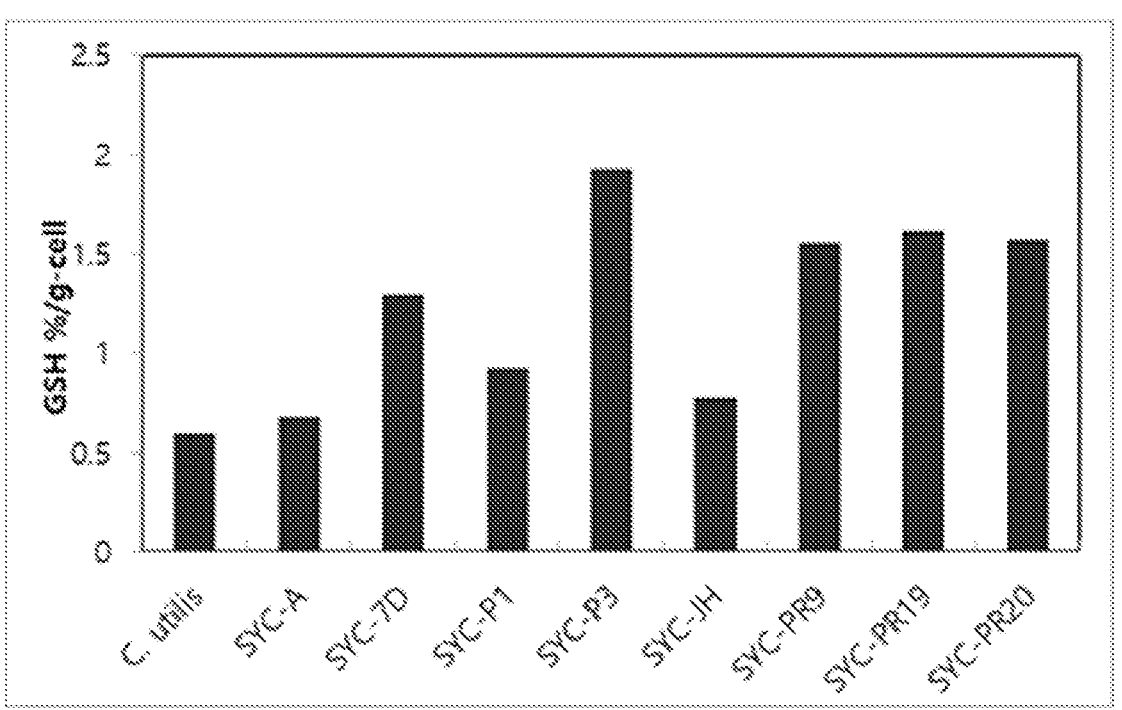

【Fig. 2】
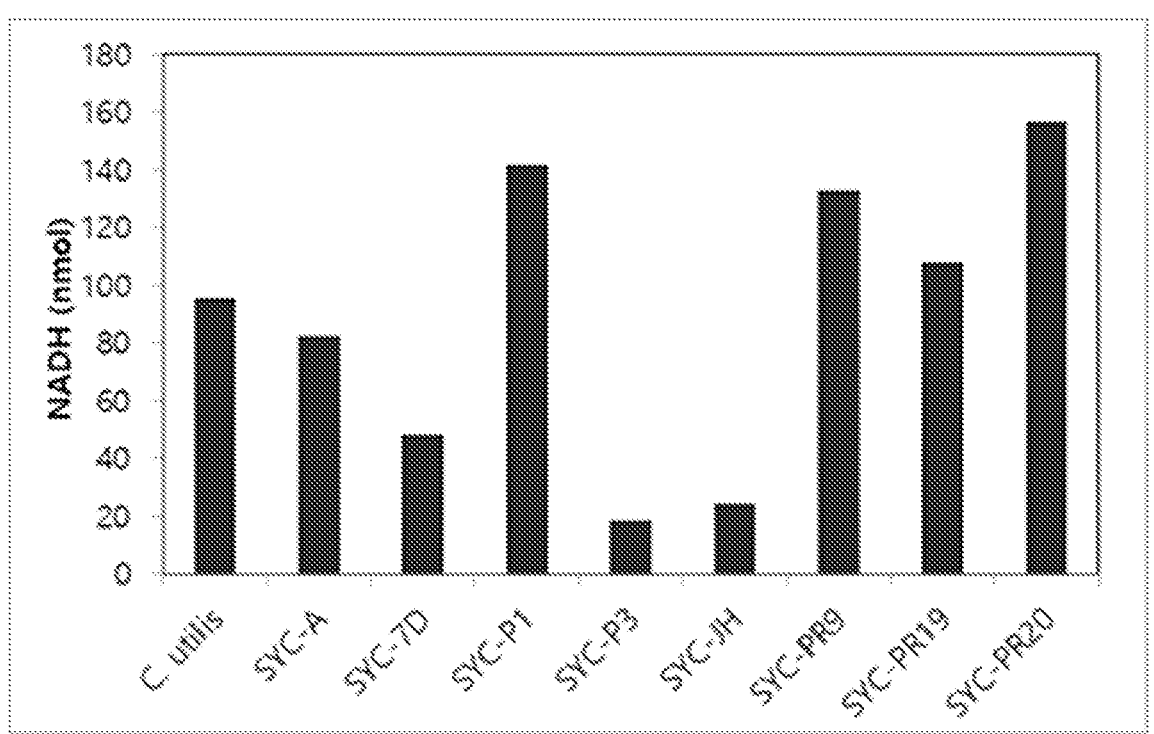

【Fig. 3】
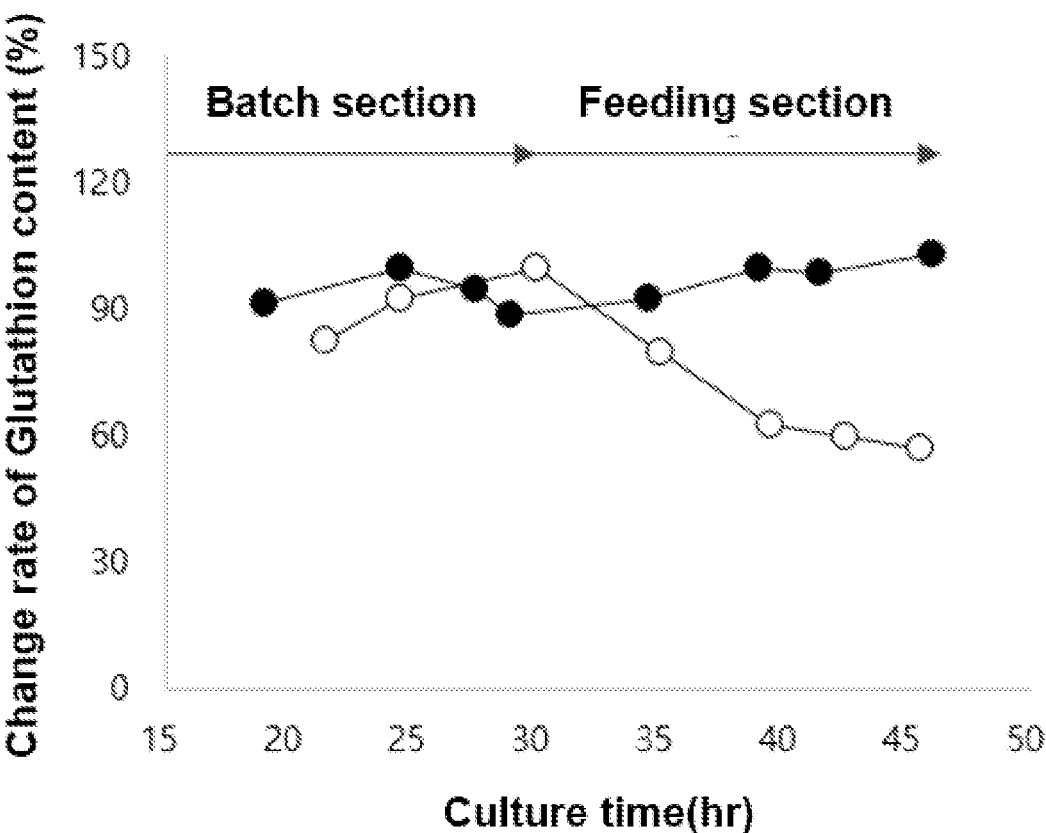

【Fig. 4】
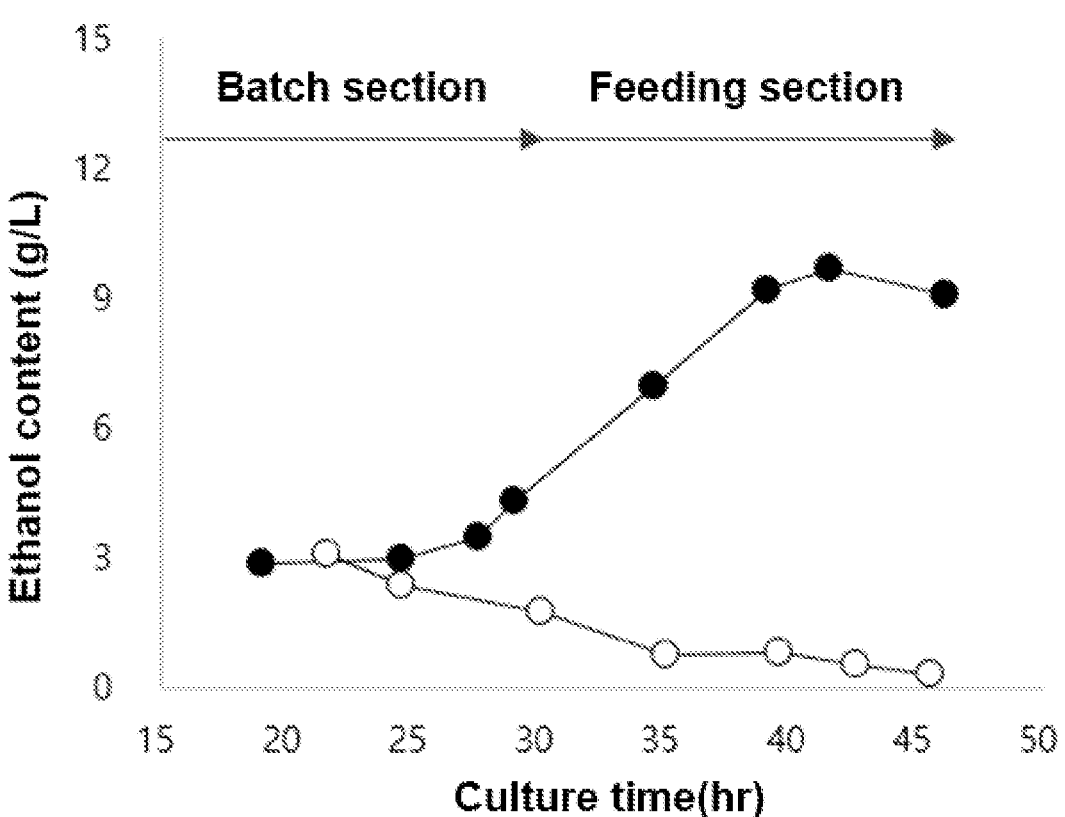

【Fig. 5】
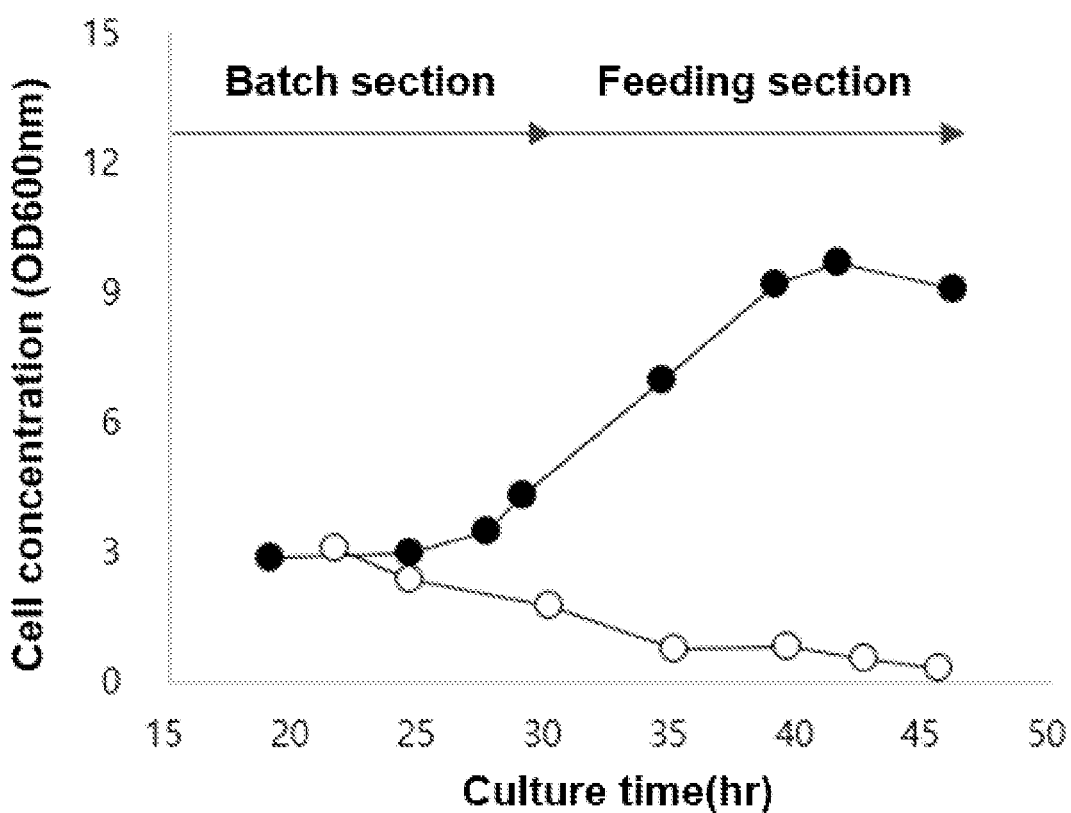

SEQUENCE LISTING

```
<160> NUMBER OF SEQ ID NOS: 3

<210> SEQ ID NO 1
<211> LENGTH: 473
<212> TYPE: DNA
<213> ORGANISM: Artificial Sequence
<220> FEATURE:
<223> OTHER INFORMATION: 18S rDNA of Candida utilis

<400> SEQUENCE: 1
acctgggcct gcgcttctag cgcggctcca accaatacac agtgtatttt gcttcttttg      60
ctttggctct gccaaaggtt ttaaacacag aaatttattt tctctagaaa ctagtcaatt     120
tgaattttaa tcttcaaaac tttcaacaac ggatctcttg gttctcgcaa cgatgaagaa     180
cgcagcgaaa tgcgatacgt aatgtgaatt gcaggttttc gtgaatcatc gaatctttga     240
acgcatattg cgctctctgg cattccagag agcatgcctg tttgagcgtc atttctctct     300
caagatcctc taggggactt ggtattgagt gatactctgt gttaacttga aatactctag     360
gcagagctcc ccctagaaat cctctgggcc gaaataatgt attaggttct accaactcgt     420
tattttccag acagacttcc aggcagagct cggctgaaca acctttctaa gct            473

<210> SEQ ID NO 2
<211> LENGTH: 19
<212> TYPE: DNA
<213> ORGANISM: Artificial Sequence
<220> FEATURE:
<223> OTHER INFORMATION: Forward primer ITS1

<400> SEQUENCE: 2
tccgtaggtg aacctgcgg                                                   19

<210> SEQ ID NO 3
<211> LENGTH: 19
<212> TYPE: DNA
<213> ORGANISM: Artificial Sequence
<220> FEATURE:
<223> OTHER INFORMATION: Backward primer ITS4

<400> SEQUENCE: 3
tccgtaggtg aacctgcgg                                                   19
```

MICROORGANISM WITH HIGH TRIPEPTIDE PRODUCTIVITY AND USE THEREOF

TECHNICAL FIELD

The present invention relates to a *Candida utilis* strain having high tripeptide-producing ability and/or alcohol lyase activity and its use.

RELATED ART

Alcohol, unlike other foods, is a kind of Xenobiotics that cannot be accumulated in the body, and its breakdown products, such as acetaldehyde are known to be a major cause of oxidative stress-induced cellular damage and hangover symptoms. Alcohol affects the liver metabolism depending on the intake amount, but the nicotinamide dinucleotide phosphate (NADP) and acetaldehydes produced in the oxidation process rather than the alcohol itself act as the main mediators of liver damage through the condensation reaction with the active amines in a body, and the acetaldehydes, which was delivered to the brain, is known to be changed into many harmful compounds, causing hangover symptoms such as hot flashes, pulse increase, nausea, and vomiting.

80 to 90% of alcohol entering the body is first decomposed into acetaldehyde by alcohol dehydrogenase (ADH) in liver cells, and then metabolized by aldehyde dehydrogenase (ALDH) to form acetic acid, which is then hydrolyzed into carbon dioxide and water for the complete decomposition. The conversion of ADH to acetaldehyde through the oxidation reaction of ethanol in the liver is an important step. An important step in the breakdown of ethanol in the liver is the conversion of ethanol to acetaldehyde through the oxidation reaction by ADH.

Glutathione (L-γ-glutamyl-L-cysteinylglycine, GSH) is a bioactive substance present in cells and is in the form of a tripeptide composed of three amino acids: glutamate, cysteine, and glycine. In the body, it exists in two forms: reduced glutathione (GSH) and oxidized glutathione (GSSG). Glutathione is found in the cells of animals, plants, and microorganisms at concentrations of 0.1 to 10 mM, and accounts for 90% or more of the total non-proteinaceous activity of cells. The diverse functions of glutathione are important not only in agriculture but also in many fields of medicine, including enzymology, transport, pharmacology, therapy, toxicology, endocrinology and microbiology.

Glutathione can be produced mainly by fermentation using microorganisms or enzymatic synthesis process. Due to the current high production cost, the enzymatic synthesis process has not yet been commercially available, whereas the method of culturing microorganisms and extracting them from microbial cells is widely used in industrial field. As a microbial strain for producing glutathione, yeast, which contains high intracellular glutathione and is recognized as a safe microorganism for food production, has been widely used. In particular, strains of the genus *Saccharomyces* and strains of the genus *Candida* are representative. In case of the wild-type strains of these yeast species, the already fairly high glutathione concentration, 0.1-1% of dry weight, and the advantages of high-density cell culture and rapid growth in low-cost media make fermentative production using yeast more competitive.

DETAILED DESCRIPTION OF THE INVENTION

Technical Problem

An embodiment of the present invention is to provide a *Candida utilis* strain having high ADH activity.

An embodiment of the present invention is to provide a *Candida utilis* strain having tripeptide-producing ability and high ADH activity.

Another embodiment of the present invention is to provide a composition for decomposing alcohol, comprising at least one selected from the group consisting of a cell of the *Candida utilis* strain, a culture of the strain, a lysate of the cell, a disruption of the cell, and an extract thereof.

Another embodiment of the present invention is to provide a composition for preventing, improving, or relieving hangover, comprising at least one selected from the group consisting of a cell of the *Candida utilis* strain, a culture of the strain, a lysate of the cell, a disruption of the cell, and an extract thereof.

Another embodiment of the present invention is to provide a composition for reducing oxidative stress or an antioxidant composition, comprising at least one selected from the group consisting of a cell of the *Candida utilis* strain, a culture of the strain, a lysate of the cell, a disruption of the cell, and an extract thereof.

Further embodiment of the present invention is to provide a composition for preventing, improving or treating oxidative stress-related diseases, comprising at least one selected from the group consisting of a cell of the *Candida utilis* strain, a culture of the strain, a lysate of the cell, a disruption of the cell, and an extract thereof.

Further embodiment of the present invention is to provide a food composition comprising at least one selected from the group consisting of a cell of the *Candida utilis* strain, a culture of the strain, a lysate of the cell, a disruption of the cell, and an extract thereof.

Technical Solution

The *Candida utilis* strain according to the present invention has glutathione-producing activity and/or alcohol dehydrogenase (ADH) activity, and more specifically, it has alcohol dehydrogenase activity as well as a high glutathione-producing activity, so as to having the advantage of working more efficiently to detoxify and excrete alcohol in the body. The yeast strain according to the present invention has an advantage of high usability as a non-GMO strain isolated from nature rather than a recombinant strain.

The *Candida utilis* strain of the present invention may have a glutathione production of 0.8% by weight or more and/or an ADH activity of 0.18 mU/ml or more per cell dry weight (g), preferably at least about 1.5 wt % of glutathione and/or an ADH activity of at least 0.2 mU/ml per cell dry weight (g).

The *Candida utilis* strain of the present invention has an alcohol dehydrogenase (ADH) activity and an alcohol tolerance, specifically the alcohol tolerance that can grow under the condition of ethanol concentration of 2 to 15% (v/v). More specifically, when cultured under the condition of an alcohol concentration of 6 to 15% (v/v), the *Candida utilis* strain of the present invention may have an optical density (OD) value of 120 to 200%, based on an optical density (OD) value of 100% for *Candida utilis* deposited under KCCM 11355.

The *Candida utilis* strain of present invention may has at least one characteristic selected from the group consisting of:

(i) increased glutathione production when cultured with shaking at 30° C., (ii) a lower limit of 105% or higher, 110% or higher, or 115% or higher, a upper limit of 120% or lower, or ranges combined with the lower limit and the upper limit, e.g., 105 to 120% of cell concentration (OD value at 600 nm) when cultured in sucrose-containing medium with shaking, based on based on 100% of cell concentration (OD at 600 nm) for a glucose-containing medium with shaking, or a lower limit of 105% or higher, 110% or higher, or 115% or higher, a upper limit of 150% or lower, 140% or lower, 130% or lower, or 120% or lower, or ranges combined with the lower limit and the upper limit, e.g., 105 to 150% or 110 to 140% of glutathione content (mg/L) when cultured in sucrose-containing medium with shaking, based on based on 100% of glutathione content (mg/L) for a glucose-containing medium with shaking, (iii) increased glutathione production when cultured with cysteine addition, and (iv) maintained amount of glutathione production under fed-batch culture conditions supplied at a feeding rate of 6 g/L·h-1, for example, 50 to 120% of glutathione content based on the glutathione content at the end of the batch, or 80% to 120% of glutathione content based on the maximum glutathione amount in the batch when cultured at a concentration of 2 g/L or more of ethanol content.

The present invention relates to health functional foods and food additives with alcohol decomposition activity, which can be widely used in the manufacture of foods for preventing alcoholic liver diseases, because the *Candida utilis* strain of present invention has hangover relief effect and helps liver detoxification before or after drinking, by having an alcohol tolerance and an alcohol decomposition ability.

Since the strain of present invention has excellent alcohol (ethanol) decomposing enzyme activity, it is possible to effectively suppress the absorption of ingested alcohol (ethanol), thereby preventing hepatic dysfunction, alcoholic liver disease, and alcoholic intestinal disease caused by the excessive alcohol metabolism.

Specifically, alcohol cannot be stored in the body and must be metabolized, and this metabolic process is mostly performed in the liver by alcohol dehydrogenases present in the liver. Alcohol is decomposed through acetaldehyde by these enzymes. The generated acetaldehyde is toxic to damage hepatocytes. A large amount of fatty acids produced from the alcohol metabolism results in accumulation of fat in the liver, causing alcoholic liver disease. These alcoholic liver diseases are largely classified into alcoholic fatty liver, alcoholic hepatitis, alcoholic liver fibrosis, and alcoholic cirrhosis. The mechanism causing liver damage is alcohol itself, metabolites such as acetaldehyde, immune reactions and the like. In particular, acetaldehyde acts as the main cause of liver toxicity, such as fat peroxidation, binding to cytoplasm, disruption of the electron transport chain of mitochondria, interfering with the function of microtubules, generation of substances binding to proteins, increasing collagen synthesis and the like.

In addition, since the strain of present invention has excellent glutathione-producing activity, it promotes the excretion of toxic substances generated by metabolism of ingested alcohol (ethanol) and protects hepatocytes from damage caused by harmful active oxygen, thereby preventing the occurrence of liver dysfunction, alcoholic liver and intestinal diseases.

Specifically, glutathione is an antioxidant promoting excretion of toxic substances through urine or bile, and in particular, has a function of promoting excretion of toxic substances by acting on detoxifying process of alcohol metabolites in the liver. In addition, glutathione protects hepatocytes from damage caused by harmful active oxygen. Therefore, the strain of present invention has a resistance to alcohol and an ability to decompose alcohol, so it not only prevents alcohol absorption and alcohol decomposition, but also promotes the excretion of toxic substances produced by the alcohol decomposition due to the high glutathione content in the strain, resulting in prevention of liver damage and liver disease.

The present invention relates to a food, food additive, beverage or health supplement containing an ingredient effective for reducing blood alcohol level and enhancing antioxidant activity in the body.

The strain of present invention can be cultured aerobically in a medium containing a carbon source, a nitrogen source, and an inorganic salt.

As the medium composition of the strain, the carbon source may be at least one or two selected from the group consisting of dextrin, glucose, sucrose, acetic acid, ethanol, molasses, and sulfite pulping waste solution, etc., or preferably sucrose in consideration of glutathione production. More specifically, the *Candida utilis* strain of present invention has may has at least one characteristic selected from the group consisting of (ii) 105 to 120% of cell concentration (OD value at 600 nm) in the sucrose-containing medium with shaking, based on 100% of cell concentration (OD) when cultured in a glucose-containing medium with shaking, or 105 to 150% or 110 to 140% of glutathione content (mg/L) in sucrose-containing medium with shaking, based on 100% of the glutathione content (mg/L) when cultured in a glucose-containing medium with shaking, (iii) increased glutathione production when cultured with cysteine addition, and (iv) maintained amount of glutathione production under fed-batch culture condition supplied at a feeding rate of 6 g/L·h-1.

The nitrogen source may be at least one or two selected from the group consisting of urea, ammonia, ammonium sulfate, inorganic salt such as ammonium chloride or ammonium phosphate, and nitrogen-containing organic materials such as corn steep liquor (CSL), casein, yeast extract, or peptone. In addition, a phosphate component, a potassium component, or a magnesium component may be added to the medium, and their examples may be ordinary industrial materials such as lime superphosphate, ammonium phosphate, potassium chloride, potassium hydroxide, magnesium sulfate, and magnesium hydrochloride. In addition, inorganic salts such as zinc, copper, manganese, iron ions and the like may be used. Other than them, vitamins, nucleic acid-related substances, and the like may be added.

The culture temperature applicable to the present invention may be culture conditions for yeast, for example 20 to 40° C., preferably 25 to 35° C., and pH 3.5 to 8.0, particularly 4.0 to 6.0.

As a culture method applicable to the present invention, any of batch culture, fed-batch culture or continuous culture may be used, but fed-batch culture or continuous culture is employed industrially.

The present invention provides a method for increasing amount of glutathione production by culturing the *Candida utilis* strain.

The culture of the strain can be performed as sugar or glucose as a carbon source. Culturing the strain may be performed by measuring an ethanol content in fermentation broth and adjusting a supply rate of carbon source. For example, when the ethanol content in fermentation broth is 5 g/L or less, the carbon source may be continuously supplied at carbon source supply rate of 5 to 10 $g/L^{\cdot h-1}$, 5.5 to 8 $g/L^{\cdot h-1}$, 5.5 to 7 $g/L^{\cdot h-1}$, or 5.5 to 6.5 $g/L^{\cdot h-1}$.

More specifically, the *Candida utilis* strain of present invention is preferably cultured by fed-batch culture in consideration of glutathione production. More preferably, the amount of produced glutathione can be maintained under the condition of fed-batch culture supplied at a feeding rate of 6 $g/L \cdot h^{-1}$.

Preferably, the method for increasing amount of produced glutathione can be performed according to at least one method selected from the group consisting of controlling carbon source type, carbon source supply rate, cysteine addition, and other culture conditions. For example, the method may be at least one method selected from the group consisting of (i) cysteine addition culture, (ii) use of sucrose or glucose as a carbon source, (iii) control of the carbon source supply rate, (iv) culture temperature, and (v) stirring condition, etc. Specifically, at least one method selected from the group consisting of shaking culture at 30° C., use of sucrose as a carbon source under shaking culture condition, cysteine addition culture, and fed-batch culture may be used. The fed-batch culture may be performed by measuring the ethanol content in fermentation broth and adjusting the carbon source supply rate, and for example, the fed-batch culture can be performed with supplied at a carbon source feeding rate of 6 g/L·h-1.

According to the method of present invention, the culture containing yeast cells including a high concentration of glutathione, and may be processed for obtaining a glutathione-containing fraction. As a method for fractionating a glutathione-containing fraction from the culture solution, any method may be used as long as it is a commonly used method, and the examples include hot water extraction, extraction by cell disruption, and the like. In addition, it is also possible to concentrate a fraction containing glutathione at a high concentration by supporting the obtained extract on a carrier. In addition, a yeast extract can also be produced from the culture obtained by the above culturing method. As a method for preparing the yeast extract, any method may be used as long as it is a usual method, and an auto-digestion method, an enzymatic decomposition method, or an alkali extraction method is industrially applied.

In addition, dried cells can be obtained from culture solution cultured by the above method. As a method for preparing the dried yeast cells, any method may be used as long as it is a method being usually performed, but a freeze-drying method, a spray drying method, a drum drying method, etc. are employed industrially.

An embodiment of the present invention is to provide a composition reducing an oxidative stress, an antioxidant composition, or a composition for preventing, improving, alleviating or treating oxidative stress-related diseases, comprising at least one selected from the group consisting of a cell of the *Candida utilis* strain, a culture of the strain, a lysate of the cell, a disruption of the cell, and an extract thereof. The composition may be a pharmaceutical composition, a food composition or a cosmetic composition.

The present invention is directed to a use of *Candida utilis* as an antioxidant being applicable newly for the treatment of disorders, conditions, pathologies and diseases resulting from or related to the adverse effects of oxidative stress and/or the production of free radicals in cells, tissues and organs of the body.

Oxidative stress causes damage to proteins, DNA and lipids and plays a critical role in the progression of neurodegenerative and age-related diseases. Hydrophobic antioxidant compounds with a low molecular weight, for example acute respiratory distress syndrome, amyotrophic lateral sclerosis, atherosclerotic cardiovascular disease, multiple organ dysfunctions, and peripheral systemic symptoms of central nervous system neurodegenerative diseases, such as Parkinson's disease, Alzheimer's disease, and Creutzfeldt-Jakob's disease. Oxidative stress is known to be causally implicated in the pathogenesis of Parkinson's disease, Alzheimer's disease and Creutzfeldt-Jakob disease, as well as other types of diseases.

The deficiency of antioxidants in cells generates excessive free radicals, so as to cause giant cell destruction, lipid peroxidation, and toxin accumulation, which can eventually lead to cell death. Because of the importance of antioxidant compounds in preventing cellular oxidation, tissues are continuously provided with natural antioxidants, such as glutathione (GSH) ([γ]-glutamyl cysteinyl glycine). GSH is synthesized in almost all cells and is one of the basic cellular antioxidants responsible for maintaining the proper oxidation state in the body. When oxidized, GSH forms a dimer called GSSG, which is recycled in the organ that produces glutathione reductase. In human adults, reduced GSH is basically produced from GSSG in the liver, and is synthesized in relatively small amounts in skeletal muscle and red blood cells and white blood cells, and is also transported to other tissues in the body through the bloodstream.

However, under certain conditions, the normal physiologic supply of GSH is insufficient, its distribution is inadequate, or excessive local oxidative demand makes it unable to prevent cellular oxidation. In other conditions, production and demand for cellular antioxidants such as GSH are mismatched, resulting in insufficient concentrations of these molecules in the body. In other cases, antioxidants are depleted by some tissue or biological pathway, which suppresses intracellular antioxidant concentrations. In any of these cases, the increased serum concentrations of antioxidants such as glutathione increases the amount of antioxidants that can enter into cells. For increased transport systems for cellular uptake, the concentration gradient leading to uptake of antioxidants is increased.

The present invention is used for the prevention, amelioration or treatment of symptoms, diseases, disorders or pathological conditions associated with overproduction of antioxidants, wherein said symptoms, diseases, disorders or pathological conditions are AIDS, diabetes mellitus, macular degeneration, congestive heart failure, cardiovascular disease, coronary artery restenosis, lung disease, inflammatory disease, asthma, RNA virus infection, DNA virus infection, sepsis, osteoporosis, bone disease, microbial infection, toxin exposure, radiation exposure, burn trauma, prion disease, neurological disease, blood disease, blood corpuscle disease, arterial disease and muscle disease.

The glutathione-containing yeast extract refers to an cell extract, and is rich in glutathione, a tripeptide composed of three amino acids, glutamic acid, cysteine, and glycine. In the composition for preventing or treating hangover according to the present invention, it is preferable to use gluta-thione-containing yeast extract containing 5% or more of glutathione.

The food composition according to the present invention may be any food or beverage to which dry yeast or yeast extract can be added, but examples thereof include alcoholic beverages, soft drinks, fermented food seasonings, soups, general foods, confectionery, and the like. Therefore, the present invention can produce efficiently the food and bev-erage containing glutathione in high concentration.

An embodiment of the present invention is to provide a composition for decomposing alcohol; a composition for preventing, improving, alleviating or relieving hangover; or a composition for preventing, improving, relieving or treat-ing alcoholic liver disease, comprising at least one selected from the group consisting of a cell of the *Candida utilis* strain, a culture of the strain, a lysate of the cell, a disruption of the cell, and an extract thereof. The alcoholic liver disease includes, but is not limited to, alcoholic fatty liver, alcoholic hepatitis, alcoholic liver fibrosis, and alcoholic cirrhosis. The composition may be a pharmaceutical composition or a food composition.

The *Candida utilis* strain of present invention has an alcohol tolerance and an alcohol decomposition activity, and thus, helps the hangover relief effect and detoxification of the liver due to alcohol decomposition before or after drinking. The present invention can provide a pharmaceu-tical composition, a food composition, a health functional food and a food additive capable of preventing, reducing, improving, alleviating or treating alcoholic liver disease using the microbial cells of the strain and the like.

In addition to the main components, the hangover-related composition of the present invention may further include vitamins such as vitamin B group, vitamin C, vitamin E, or beta-carotene, mineral components such as Ca, Mg, or Zn, phospholipids such as lecithin, amino acids such as alanine or taurine, fructose, oligosaccharide, *Ganoderma lucidum*, or mixtures thereof, as auxiliary components. The ingredi-ents such as amino acids contained in the yeast extract have a function of promoting alcohol metabolism, thereby reliev-ing, improving, or preventing a hangover.

The *Candida utilis* strain of present invention has resis-tance to alcohol and alcohol decomposition ability, so it can prevent alcoholic liver disease beforehand by helping the hangover relief effect and detoxification of the liver before or after drinking. Since the strain of present invention has excellent activity of alcohol (ethanol) degrading enzyme, it effectively suppresses an absorption of ingested alcohol (ethanol), thereby preventing liver dysfunction caused by excessive alcohol metabolism, alcoholic liver disease, and alcoholic intestinal disease. Furthermore, since the strain of present invention produces glutathione, it can prevent, improve, or reduce liver toxicity caused by toxic substances generated in the alcohol metabolism process, as well as promote excretion of alcohol metabolites.

The pharmaceutical composition according to the present invention can be prepared in a conventional formulation form by selecting and adding pharmaceutically acceptable carriers and additives in addition to the active ingredients. The pharmaceutical composition may be formulated into a formulation of a solution, suspension, powder, granule, tablet, capsule, pill, or extract so as to be taken orally, but is not limited thereto. The pharmaceutically acceptable carrier may be selected from one or more of diluents, lubricants, binders, disintegrants, sweeteners, stabilizers, and preserva-tives, and pharmaceutically acceptable additives include at least one selected from the group of consisting of flavoring agents, coloring agents, antifriction, and acidulants.

In addition, as an additive to enhance the taste, natural flavors such as plum flavor, lemon flavor, pineapple flavor, and herb flavor, natural pigments such as natural fruit juice, chlorophyllin, and flavonoids, sweet ingredients such as fructose, honey, sugar alcohol, and sugar, and acidulants such as citric acid and sodium citrate.

In order to obtain an effect of preventing or treating hangover, the pharmaceutical composition may be admin-istered orally several times so that the total amount per day is 0.3 to 10 g, preferably 0.7 to 4.2 g based on an active ingredient for an adult with 60 kg body weight, but is limited thereto. It can be used in an appropriate amount for the desired effect, but not limited thereto.

In addition, the composition of the present invention may be used as a health supplement. These health supplements can be made into teas using extracts as active ingredients, jellies, liquid extracts, beverages, etc.

Effect of the Invention

The present invention relates to *Candida utilis* strain having a tripeptide-producing ability and/or a high ADH activity, a composition for decomposing alcohol, a compo-sition for relieving, improving or preventing hangover, or a composition for relieving oxidative stress, or an antioxidant composition.

BRIEF DESCRIPTION OF THE DRAWINGS

FIG. 1 is a graph showing glutathione productivity of candidate strains primarily selected according to the present invention.

FIG. 2 is a graph showing the concentration of NADH produced per unit time of the candidate strains primarily selected according to the present invention.

FIG. 3 is a graph showing a change rate of glutathione content depending on the sucrose supplying rate according to the present invention.

FIG. 4 is a graph showing an ethanol content in the culture medium depending on the sucrose supplying rate according to the present invention.

FIG. 5 is a graph showing the change in cell concentration over time according to the sucrose supplying rate according to the present invention.

DETAILED DESCRIPTION OF THE EMBODIMENTS

The present invention will be described in more detail with reference to the following examples, but the present invention is not intended to be limited to the following examples.

Example 1: Isolation of Microorganism Producing Glutathione 1-1: Microorganism Culture To screen microorganisms producing glutathione, rice wine (Makgeolli) koji, and traditional sources were pur-chased at traditional markets across the country and were used them as samples. 1 g of the sample was suspended in 10 mL of 0.85% NaCl, and 100 µl of the suspension was plated on a YPD (Yeast extract 10 g/L, Peptone 20 g/L, Dextrose 20 g/L) agar plate and the solid culture was performed at 30° C. for 2 days. Among the colonies grown on the solid medium, 150 colonies were isolated by selecting those with different shapes and sizes, and then cultured at 30° C. for 2 days in a test tube containing YPD broth (yeast extract 10 g/L, Peptone 20 g/L, Dextrose 20 g/L) with agitation, to obtain the cell culture.

1-2: Measurement of Cell Growth Degree (Absorbance)

The cell concentration was determined by measuring the absorbance at 600 nm for the cell culture, and the result was represented as the cell optical density (OD) value.

1-3: Measurement of Glutathione Content in the Culture

The cell culture solution was centrifuged to remove the supernatant, and the microbial cells were collected by washing with distilled water once. The collected cells were added with 40~70% ethanol, and the intracellular glutathione was extracted using a fine mixer for 10~30 minutes. After centrifugation of the extraction solution, the supernatant was taken and reacted with 10 mM DTNB (5,5'-Dithiobis-(2-Nitrobenzoic Acid) dissolved in 0.5 M potassium phosphate at pH8.0 buffer for 20 min at 40° C., and the glutathione content (GSH mg/L) was determined by measuring the absorbance at 412 nm. DTNB, commonly used for glutathione content analysis, is known as Ellman's reagent designed to detect thiol compounds. The reaction of GSH with DTNB produces y2-nitro-5-benzoic acid and GSSG, and the concentration of GSH can be calculated by measuring the OD value at 412 nm. GSH is prepared from GSSG by glutathione reductase, and reacts with DTNB again, to form a recycling system.

1-4: Measurement of Glutathione Content Per Cell Dry Weight (g)

The cell culture solution was centrifuged to remove the supernatant, and the microbial cells were collected by washing with distilled water once. The absorbance was measured for the collected cells, and the dried cell weight was calculated according to the absorbance. Specifically, in order to measure the cell dry weight (g), the cell culture solution was centrifuged to remove the supernatant, and the microbial cells were collected only. The collected cells were washed with 0.9% NaCl and diluted with distilled water to prepare samples with 0.1 to 1 of absorbance.

The absorbance was measured at 600 nm for the diluted cell samples, and the dry cell weight was calculated according to the absorbance. After measuring the absorbance, the cells were filtered under reduced pressure with a 0.2 μm filter paper. The filter paper with cells remaining was dried at 60° C. for more than 12 hours, left in a desiccator containing silica gel for more than 6 hours, and then the cell weight was measured. The amount of dried cells was determined by calculating the weight difference between the empty filter paper and the filter paper with the cells filtered out. Therefore, it was possible to determine the dry cell concentration (g/L) according to the absorbance value.

After measuring the absorbance, glutathione was extracted from the cells in substantially the same manner as in Examples 1-3, and the extraction solution was centrifuged to take the supernatant, and then the produced amount of glutathione (g/L) was measured. The measured amount of glutathione was divided by the calculated dry cell weight (g/L) and then multiplied by 100 to calculate GSH % per dry cell weight (g). The glutathione content per dry cell weight (g) was measured, and shown in Table 1 as GSH (%)/g-cell.

As a result of measuring the glutathione productivity of 150 strains by the method, the glutathione production per cell dry weight (g) (GSH (%)/g-cell) ranges about 0.3 to 2% by weight. The top seven (70 candidate strains were isolated based on the glutathione content per sugar. As a result of the analysis of the selected 7 strains, the cell OD of Example 1-2, the glutathione content of Example 1-3, and the glutathione content per cell dry weight (g) are shown in Table 1, and the cell dry weight (g) Glutathione content per sugar is shown in FIG. 1.

As a control, the same experiment was performed on the standard strain of *C. utilis* KCCM 11355, and the results are shown in Table 1 and FIG. 1.

TABLE 1

| Sample | Cell growth(O.D) | glutathione content (GSH mg/L) | glutathione productivity GSH(%)/g-cell |
|---|---|---|---|
| Control group | 18.0 | 46 | 0.6 |
| SYC-A | 18.0 | 49 | 0.7 |
| SYC-7D | 14.3 | 74 | 1.3 |
| SYC-P1 | 19.9 | 73 | 0.9 |
| SYC-P3 | 17.5 | 135 | 1.9 |
| SYC-JH | 20.9 | 65 | 0.8 |
| SYC-PR9 | 18.0 | 112 | 1.6 |
| SYC-PR19 | 17.0 | 110 | 1.6 |
| SYC-PR20 | 17.8 | 112 | 1.6 |

As shown in Table 1, as a result of analyzing cell growth and glutathione production in an ethanol-free medium, the glutathione contents of the seven selected strains were higher than that of the standard strain *C. utilis* KCCM 11355, specifically about 0.7 to 2% by weight. The six strains except for SYC-7D strain, had the same or higher degree of cell growth than that of the standard strain, and thus had more desirable characteristics.

Therefore, considering glutathione production (mg/L) and glutathione production per dry cell weight (GSH (%)/g-cell) as strain selection criteria, SYC-7D, SYC-JH, SYC-P1, SYC-P3, SYC-PR9, SYC-PR19, and SYC-PR20 could be selected. Preferably SYC-7D, SYC-JH, SYC-P1, SYC-P3, SYC-PR9, SYC-PR19, and SYC-PR20 having 0.8% by weight or more of the glutathione production per cell dry weight (g) (GSH (%)/g-cell), or more preferably, SYC-PR9, SYC-PR19, and SYC-PR20 having 1.5% by weight or more of the glutathione production per cell dry weight (g) (GSH (%)/g-cell) could be selected.

In particular, when considering industrial mass production, it is more preferable to consider both the cell OD value and the produced amount of glutathione per dry cell weight (GSH (%)/g-cell). From this point of view, it was confirmed that the strains SYC-P1, SYC-PR9, SYC-PR19, and SYC-PR20 having higher cell OD values and higher glutathione production than the standard strains were more preferable.

Example 2: Alcohol Dehydrogenase (ADH) Activity Assay

The ADH activity was measured by culturing the seven (7) strains with high glutathione content selected in Example 1.

Specifically, the ADH activity was analyzed using an ADH Activity Assay Kit (Abcam). After culturing for 24 to 48 hours at 30° C. in YPD medium, the cells were collected to 1×10⁶ CFU/ml. The collected cells were washed with distilled water, and then were added with ADH assay buffer, to disrupt the cell walls using a bead beater. As the composition of the reaction solution, 50 μl of sample or NADH standard material was mixed with 82 μl of ADH assay buffer, 8 μl of Developer, and 10 μl of Isopropanol for each concentration. After reacting at 37° C. for 3 minutes, the absorbance of the experimental group (A0) and the control group was measured at 450 nm. After an additional reaction at 37° C. for 30 minutes, the change in absorbance at 450 nm was measured, and the amount of NADH produced per unit time (minute) was calculated to compare the ADH activity of each strain. The amount of NADH production for each strain measured is shown in FIG. 2. It was confirmed that the 7 strains had NADH production in the range of 24 to 160 nmol. As a control, the same experiment was performed for the standard strain of *C. utilis* KCCM 11355, and the results are shown in Table 2.

TABLE 2

| sample | ADH Activity (mU/ml) |
|---|---|
| Control group | 0.16 |
| SYC-A | 0.14 |
| SYC-7D | 0.08 |
| SYC-P1 | 0.24 |
| SYC-P3 | 0.03 |
| SYC-JH | 0.04 |
| SYC-PR9 | 0.22 |
| SYC-PR19 | 0.18 |
| SYC-PR20 | 0.26 |

As shown in Table 2, the ADH activity of the 7 selected strains ranged from 0.03 to 0.26 mu/ml, and the strains having higher ADH activity that that of the standard strain *C. utilis* KCCM 11355 (control) were SYC-P1, SYC-PR9, SYC-PR19 and SYC-PR20, and the strain showing the highest activity was identified as SYC-PR20. Accordingly, in terms of ADH activity, SYC-P1, SYC-PR9, SYC-PR19, and SYC-PR20 could be selected secondarily. Preferably, SYC-P1, SYC-PR9, and SYC-PR20 having an ADH activity of 0.20 (mU/ml) or more could be selected. In consideration of combining the glutathione content per dry cell weight (g) shown in Table 1 of Example 1, and the ADH activity analysis results in Table 2, the strains with high glutathione production and ADH activity are preferred. Accordingly, SYC-PR9, SYC-PR19, and SYC-PR20 can be selected as secondary candidate strains.

Example 3: Evaluation of Cell Growth and GSH Production Depending on Culture Time For SYC-PR20 selected in Example 1, cell growth and GSH production were evaluated according to the culture time.

YPD (yeast extract 10 g/L, Peptone 20 g/L, Dextrose 20 g/L) medium was prepared as a medium for culturing the SYC-PR20 strain. 3 ml of medium was dispensed into a test tube, and the culture was performed for a culture time of 24 to 60 hours at 30° C. with agitation. The culture solution was taken at 24 hours, 36 hours, 48 hours, and 60 hours, respectively, and cell OD value, glutathione content, and Glutathione content per cell dry weight (g) were measured, and the results are shown in Table 3 below.

TABLE 3

| Culture time(hour) | Cell growth(O.D) | glutathione content (GSH mg/L) | Glutathione productivity GSH(%)/g-cell |
|---|---|---|---|
| 24 | 12 | 69 | 1.4 |
| 36 | 15 | 82 | 1.4 |
| 48 | 18 | 111 | 1.6 |
| 60 | 19 | 120 | 1.6 |

As a result of measuring the cell O.D value and GSH production from 24 hours to 60 hours of incubation time of the strain, the cell O.D increased from 12 at 24 hours, 15 at 36 hours, 18 at 48 hours, and 19 at 60 hours. It was confirmed that the production of GSH was 69 at 24 hours, 82 at 36 hours, 111 at 48 hours, and 120 mg/L at 60 hours. Therefore, it was confirmed that the GSH % per g of cell dry weight increased from 1.4% at 24 hours to 1.6% at 60 hours.

Example 4: Evaluation of Microorganism's Tolerance to Ethanol

For SYC-PR20 selected in Example 1, cell growth was evaluated in an ethanol-containing medium.

Specifically, a 5×YPD (yeast extract 50 g/L, Peptone 100 g/L, Dextrose 100 g/L) medium was prepared and mixed with 100% ethanol to make the final ethanol concentration in the medium to be 0, 2, 4, 6, 8, 10, or 15 v/v %. 3 ml of the medium containing ethanol for each concentration was dispensed into a test tube and cultured with shaking at 30° C. for 60 hours to obtain culture solution. For the culture solution, the cell concentration was analyzed by measuring the absorbance at 600 nm in substantially the same manner as in Example 1-2, and the results are shown in Table 4 below.

As a control, the same experiment was performed on the standard strain of *C. utilis* KCCM 11355, and the results are shown in Table 4.

TABLE 4

| | Ethanol(v/v %) | | | | | | |
|---|---|---|---|---|---|---|---|
| | 0 | 2 | 4 | 6 | 8 | 10 | 15 |
| OD value of control group | 18.0 | 13.9 | 12.2 | 9.3 | 2.8 | 1.2 | 0.5 |
| Relative OD value of control group to ethanol-free medium | 100.0% | 77.2% | 67.8% | 51.7% | 15.6% | 6.7% | 2.8% |
| OD value of SYC-PR20 | 19 | 15.8 | 13.6 | 11.0 | 4.2 | 2.1 | 0.8 |
| Relative OD value of SYC-PR20 to ethanol-free medium | 100.0% | 81.0% | 69.7% | 56.4% | 21.5% | 10.8% | 4.1% |
| Relative OD value of SYC-PR20 to control group (%) | 108.3% | 113.7% | 111.5% | 118.3% | 150.0% | 175.0% | 160.0% |

*Saccharomyces* cerevisiase, known as a strain with high alcohol tolerance, can grow at ethanol concentrations of 7-11% (v/v). The SYC-PR20 strain, which was secondly selected according to Examples 2 and 3, had high alcohol tolerance and, in particular, exhibited high cell growth in an alcohol-containing medium compared to the standard strain of *C. utilis* KCCM 11355 (control group), particularly high cell growth of 110% or more at an ethanol concentration of 0.5 to 15 v/v %.

In Table 4, the SYC-PR20 strain having a relatively high ADH activity had a higher cell concentration at the same ethanol concentration than the control group. Accordingly, it was confirmed that the SYC-PR20 strain had excellent glutathione production ability, ADH activity and alcohol tolerance.

Example 5: Strain Identification

In Example 4, the SYC-PR20 strain showed the most preferable characteristics among the 7 selected strains with a glutathione yield of 1.6% and an ADH activity of 0.26 mU/ml.

The SYC-PR20 strain was subjected to 18S rRNA sequence analysis by using universal primers ITS1 (SEQ ID NO: 2: 5'-TCCGTAGGTGAACCTGCGG-3') and ITS4 (SEQ ID NO: 3: 5'-TCCGTAGGTGAACCTGCGG-3'). The 18S rDNA sequence of the SYC-PR20 strain is shown in SEQ ID NO: 1. As a result of strain identification based on the 18S rDNA sequence, it was identified as *Candida utilis* (*Pichia jadinii*).

The *Candida utilis* SYC-PR20 strain was deposited at the Korean Culture Center of Microorganism, located at 45, Hongjenae 2ga-gil, Seodaemun-gu, Seoul, on Aug. 7, 2020, and received accession number of KCCM 12777P.

Example 6: Evaluation of Glutathione Productivity on Fermenter Culture

In the flask culture conditions such as Examples 1-4 for the isolation and characterization of microorganisms, it is difficult to increase the agitation speed beyond a certain level due to mechanical limitations, and to control a constant culture environment (air amount, pH, etc.). On the other hand, in industrial scale culture, by supplying air to the culture medium and performing agitation, medium components and oxygen are uniformly distributed in all spaces, and temperature, pH, etc. can be adjusted, thereby enabling cell culturing under optimized conditions. Accordingly, the fermenter culturing shows a higher cell growth rate than the flask culturing, and thus, the consumption of the added sugar occurs quickly and the productivity increases. Therefore, fermenter culturing experiments for industrial application of the microorganism are required.

Specifically, the colony formed on YPD agar plate inoculated with the *Candida utilis* SYC-PR20 strain according to Example 5 was inoculated into 3 mL of YPD (Yeast extract 10 g/L, Peptone 20 g/L, Dextrose 20 g/L) broth, cultured for 24 hours at a temperature of 30° C. and 240 rpm to obtain the seed culture, and 3 mL of the previously cultured seed culture was inoculated into 100 mL of the same YPD broth and cultured under the same conditions to prepare a seed culture for a 5 L fermenter.

In order to evaluate cell growth and glutathione production according to carbon sources, 5 L fermenter culturing was performed. Specifically, a glucose-based culture medium and a sucrose-based culture medium were prepared in a final 2 L culture volume in a 5 L fermenter with the medium composition shown in Table 5, respectively. The prepared seed culture for 5 L fermenter culturing was inoculated into a 5 L fermenter and cultured while stirring under the conditions shown in Table 6.

TABLE 5

| glucose-based culture medium | | sucrose-based culture medium | |
|---|---|---|---|
| component | Content (g/L) | component | content (g/L) |
| Glucose | 30 | Sucrose | 30 |
| MgSO4-7H2O | 0.5 | MgSO4-7H2O | 0.5 |
| Yeast extract | 3.75 | Yeast extract | 3.75 |
| Corn steep Powder | 5.25 | Corn steep Powder | 5.25 |
| Methionine | 4 | Methionine | 4 |
| (NH4)Cl2 | 10 | (NH4)Cl2 | 10 |
| KH2PO4 | 2 | KH2PO4 | 2 |
| K2HPO4 | 2 | K2HPO4 | 2 |
| NaCl | 0.5 | NaCl | 0.5 |

TABLE 6

| Culture condition | Primary seed culture | Seed culture | Main culture |
|---|---|---|---|
| Volume | 3 mL | 100 mL | 2 L |
| Temperature | 30° C. | 30° C. | 28° C. |
| Agitation speed | 240 rpm | 240 rpm | 500 rpm |
| Culturing pH | Not control | Not control | 5.0 |
| Culturing time | 24 hr | 24 hr | 29 hr |

Cell concentration and glutathione production of the obtained culture solution were measured in substantially the same manner as in Example 1, and the measurement results are shown in Table 7 below.

TABLE 7

| Culturing conditions | Culturing time(hr) | Cell O.D.(600 nm) | GSH content (mg/L) on saccharide concentration of 30 g/L | GSH content (mg/L) on saccharide concentration of 1 g/L |
|---|---|---|---|---|
| glucose-based culture medium | 29.0 | 28.4 | 182.3 | 6.08 |
| sucrose-based culture medium | 29.0 | 31.9 | 223.3 | 7.44 |

As shown in the results of Table 7, the time when the initial input saccharides was almost consumed was the end of the culture at 29 hours for both glucose and sucrose-based cultures, and OD value at 600 nm as the cell concentration at that time was 28.4 for glucose-based culture and 31.9 for sucrose-based culture, to show increased cell yield for sucrose-based culture by 112%. The glutathione content was 223.3 mg/L in the sucrose-based culture, which was about 122% higher than that of the glucose-based culture in the same time culture.

Example 7: Evaluation of Glutathione Production According to Culture Conditions The colony formed on the YPD agar plate inoculated with the *Candida utilis* SYC-PR20 strain according to Example 5 was inoculated into 3 mL of YPD (Yeast extract 10 g/L, Peptone 20 g/L, Dextrose 20 g/L) broth, cultured for 24 hours at a temperature of 30° C. and 240 rpm to obtain the seed culture, and 3 mL of the previously cultured seed culture was inoculated into 100 mL of the same YPD broth and cultured under the same conditions to prepare a seed culture for a 5 L fermenter.

In order to evaluate high-concentration cells and glutathione production, the seed culture and 5 L fermenter culture were prepared as in Example 5. In batch culture, when the accumulated ethanol concentration after initial saccharide consumption was 5 g/L or lower, Fed-batch culture is performed by continuously supplying saccharide solution containing sucrose of 600 g/L to maintain high-concentration cell culture and glutathione productivity.

As a result, according to the sucrose feeding rate, the amount of change in glutathione content in the culture solution was measured over time and shown in FIG. 3, and the ethanol content in the culture solution was measured over time and shown in FIG. 4. In addition, the change in cell concentration according to the sucrose feeding rate was measure over time and shown in FIG. 5. In FIGS. 3, 4 and 5, the white sphere means a sucrose feeding rate of 4.5 g/L·h-1, and the black sphere means a sucrose feeding rate of 6 g/L·h-1.

When supplied at a sucrose feeding rate of 6 g/L·h-1, the ethanol content in the culture medium was maintained at 3 g/L or more, and accordingly, the glutathione content change rate was almost constant. On the other hand, at a low sucrose feeding rate (4.5 g/L·h-1), the ethanol content was maintained at low and the intracellular glutathione content decreased. This fact indicates that when the sucrose feeding rate is high, the energy required for glutathione biosynthesis is sufficiently supplied by sufficient saccharide supply in the culture medium, but when the sucrose feeding rate is low, the energy supply is not sufficient, resulting in limited cell growth and decreased glutathione content.

Therefore, when *Candida utilis* SYC-PR20 strain according to the present invention is supplied at a saccharide feeding rate of 6 g/L·h-1, ethanol is accumulated in the culture medium as a metabolite of the cells due to sufficient saccharide supply, and glutathione is increased to the level of batch culture in the high concentration culture section. content can be maintained, which is more preferable.

ACCESSION NUMBER

Name of depository authority: Korean Culture Center of Microorganisms
Accession number: KCCM12777P
Accession date: 20200807

---

The invention claimed is:

1. A method for increasing glutathione production, comprising culturing a *Candida utilis* strain having alcohol dehydrogenase (ADH) activity, and alcohol tolerance, and glutathione-producing ability, wherein the *Candida utilis* strain has an accession number KCCM 12777P.

2. The method of claim 1, wherein the culturing the strain is performed by using sucrose or glucose as a carbon source.

3. The method of claim 1, wherein the culturing of strain is performed by adjusting a carbon source supply rate with measuring an ethanol content in fermentation solution.

4. The method according to claim 1, wherein the strain is cultured with adding cysteine.

5. The method of claim 1, wherein the strain has an ADH activity of 0.18 mU/ml or higher per cell dry weight (g), and a glutathione production of 0.8% by weight or more per cell dry weight (g).

6. The method of claim 1, wherein the strain exhibits alcohol tolerance and is capable of growing under ethanol concentration of 2 to 15% (v/v).

\* \* \* \* \*